US00PP10923P

United States Patent [19]

Olesen et al.

[11] Patent Number: Plant 10,923

[45] Date of Patent: May 25, 1999

[54] SHRUB ROSE PLANT NAMED 'POULDRON'

[75] Inventors: Pernille Olesen; Mogens Olesen, both of Fredensboro, Denmark

[73] Assignee: Weeks Wholesale Rose Grower, Inc., Upland, Calif.

[21] Appl. No.: 08/960,794

[22] Filed: Oct. 30, 1997

[51] Int. Cl.[6] ..... A01H 5/00

[52] U.S. Cl. ..... Plt./107

[58] Field of Search ..... Plt./1, 28, 107

[56] References Cited

PUBLICATIONS

UPOV-ROM, 1998/01, Plant Variety Database, GTI Jouve Retrieval Software, Citation for 'Pouldron'.

*Primary Examiner*—Howard J. Locker

*Attorney, Agent, or Firm*—Christie, Parker & Hale, LLP

[57] ABSTRACT

A new plant variety of Shrub rose suitable for garden decoration, having flowers of coral pink coloration.

1 Drawing Sheet

BACKGROUND OF THE INVENTION

This invention relates to a new and distinct variety of Shrub rose plant. The varietal denomination of the new variety is 'Pouldron'. It has as its seed parent the variety known as 'Poulskov' (U.S. Plant Pat. No. 9,062) and an undistributed seedling as its pollen parent.

SUMMARY OF THE INVENTION

Among the features which distinguish the new variety from other presently available and known commercial rose cultivars are the following combination of characteristics: its moderately small ovoid to globular buds, its compact rounded habit with very full branching and abundant foliation, its very double flowers of coral pink coloration and its above average degree of resistance to powdery mildew and rust. The plant is a bushy compact plant, suitable for outdoor garden decoration.

Asexual reproduction of the new variety by budding as performed in Kern County and Upland, Calif. shows that the foregoing and other distinguishing characteristics come true to form and are established and transmitted through succeeding propagations. 'Pouldron' may be asexually propagated by cuttings, budding and grafting.

COMPARISON WITH PARENTS

The new rose may be distinguished from its seed parent, 'Poulskov', by the following combination of characteristics: whereas 'Poulskov' bears flowers of a light pink coloration, 'Pouldron' bears flowers of a deeper coral pink coloration; 'Poulskov' leaves are about 9 to about 10 cms. in length and about 5 to about 6 cms. in width at the widest point, whereas the leaves of the new variety are significantly larger, about 8 to about 13 cms. in length and about 6 to about 9 cms. in width at the widest point; 'Pouldron' has a mature plant height of about 70 to about 90 cms., whereas the seed parent has a significantly shorter mature height of about 65 to about 75 cms.

The new variety may be distinguished from its pollen parent, an undistributed seedling, by the following combination of characteristics: whereas 'Pouldron' bears flowers about 7 to about 8.5 cms. in diameter of very double petalage, about 44 to about 58 petals; the pollen parent bears significantly larger flowers, about 9 to about 11 cms. in diameter with significantly lower petalage, about 30 to about 37 petals. The foliage of the pollen parent is very glossy in its finish, whereas the finish on the foliage of 'Pouldron' is significantly less glossy.

BRIEF DESCRIPTION OF ILLUSTRATION

The accompanying photograph illustrates specimens of the new variety and shows the flowering thereof from bud to full bloom depicted in color as nearly correct as it is possible to make in a color illustration of the character. Throughout this specification, color values are based upon the Colour Chart of The Royal Horticultural Society of London, England, except where common terms of color definition are employed.

DESCRIPTION OF THE NEW VARIETY

The following description is of rose plants of the new cultivar grown outdoors in Upland, Calif. in the month of September. Phenotypic expression may vary with environmental, cultural and climatic conditions, as well as differences in conditions of light and soil.

Flower

The new variety bears its flowers sometimes singly, but usually in clusters of three to four or more per stem. Flowers are borne in moderately flat to somewhat rounded clusters on normal strong short to medium length stems (about 11 to about 17 cms.). Outdoors, the plant blooms very abundantly and nearly continuously during the growing season. The flowers have a slight tea fragrance.

Bud

The peduncle is about 4 to about 6.5 cms. in length, of average caliper, and usually erect. It is almost entirely smooth, with very few stipitate glands. Peduncle color is between 144B and 147B. The side facing the sun sometimes blushes with between 183B and 178B.

Before the calyx breaks, the bud is about 1.4 to about 1.7 cms. in diameter at the widest point, about 1.8 to about 2.3 cms. in length, and ovoid to globular in shape. The surface of the bud is almost entirely smooth, with very few stipitate glands and some hairs, usually with slender foliaceous parts extending beyond the tip of the bud equal to ½ or more of its length. Bud color is between 147B and 144A.

The inner surface of the sepals is covered with very fine wooly tomentum; sepal margins are lined with some stipitate glands and some hairs and one to two very slender foliaceous parts.

As the petals open, the bud is about 1.8 to about 2.2 cms. in diameter at the widest point, about 2 to about 2.5 cms. in length, and somewhat flat-topped to very globular in form. The color of the under surfaces of the newly opened petals is between 48D and 39C. At the point where the petal attaches, there is a small zone of near 4C. The color of the upper surfaces of the newly opened petals is between 48C and 39B. At the point where the petal attaches, there is a zone of between 4B and 5C.

Bloom

When fully open, the bloom ranges from about 7 to about 8.5 cms. in diameter. Petalage is very double with about 44 to 58 petals and about 7 to 10 petaloids arranged irregularly. When partially open, the bloom form is very full to cupped, and the petals are very tightly spiraled to moderately cupped with petal edges slightly reflexed outward. When fully open, the bloom form is more cupped to slightly globular, and the petals are more loosely cupped to somewhat with petal edges somewhat reflexed outward.

Petals

The substance of the petals is moderately heavy and of medium thickness, with upper surfaces slightly shiny to satiny and under surfaces mostly shiny. The outer petals are nearly round to broadly obovate in shape with apices usually rounded to sometimes slightly mucronate. The inner petals are more narrowly obovate in shape with apices usually rounded to sometimes slightly mucronate.

Newly Opened Flower

The under surface of the outer, intermediate and inner petals is between 48D and 39C. At the point where the petal attaches, there is a small zone of near 4D. The upper surface of the outer, intermediate and inner petals is between 48C and 39B. At the point where the petal attaches, there is a zone of between 4C and 5D.

The general tonality of the newly opened flower is between 48C and 39B.

Three Day Old Flower

The under and upper surface of the outer and inner petals is between 49B and 39D. At the point where the petal attaches on both the under and upper surface of the outer and inner petals, there is a small zone of near 155A.

The general tonality of the three day old flower is between 49B and 39D.

On the spent bloom, the petals sometimes persist, fading to between 49D and 36D before dropping.

In September in Upland, Calif., blooms on the bush growing outdoors generally last from about four to five or more days. Cut roses grown outdoors and kept at normal indoor living temperatures generally last from about five or more days.

Male Reproductive Organs

Stamens are average to many in number (approximately 80) and are arranged regularly about the pistil; a few are tucked in the calyx. The filaments are moderately short in length, most with anthers. The anthers are somewhat small for the class and all open approximately at the same time. Anther color is between 16B and 21C when immature and near 166C at maturity. Pollen is moderately abundant and near 16D in color.

Female Reproductive Organs

Pistils vary in number (approximately 85). The styles are somewhat uneven, moderately short in length, average in caliper, and loosely bunched. Stigma and style color is near 2C. Ovaries are usually all enclosed in the calyx.

Hips are of average length, somewhat obovoid to globular in form, and near 21C in color when ripe. The hip surface is very smooth with somewhat thick fleshy walls. There are approximately six to eleven seeds.

Foliage

The compound leaves are comprised of three to five, and sometimes seven, leaflets and are borne abundantly. The leaves are about 8 to about 13 cms. in length and about 6 to about 9 cms. in width at the widest point, somewhat leathery in texture, and semi-glossy in finish. The leaflets are about 2.5 to about 6 cms. in length and about 1.5 to about 3.8 cms. in width at the widest point, oval in shape with acute apices and somewhat round to abute bases. Their margins are usually irregularly serrate.

The upper surface of the mature leaf is between 137A and 147A. The under surface of the mature leaf is between 137D and 147B. The upper surface of the young leaf is between 137D and 147B, usually suffused with between 183B and 178B. The under surface of the young leaf is between 144A and 146C, usually heavily suffused with between 183B and 178B.

The rachis is average in caliper and moderately smooth. The upper side is moderately grooved with few stipitate glands on the edges of the grooves. Sometimes the edges of the grooves on the young leaf are suffused with between 183B and 178B. The under side of the rachis is very smooth.

The stipules are moderately long with somewhat narrow, medium length points that usually turn out at an angle of more than 45 degrees.

The plant displays an above average degree of resistance to powdery mildew and rust as compared to other commercial varieties grown under comparable conditions in Upland, Calif.

Growth

The plant has a bushy, compact, low to medium growth habit (about 70 to about 90 cms. in height and about 70 to about 85 cms. spread at the widest point), with very full branching. It displays very vigorous growth and the canes are of medium caliper.

The color of the major stems is near 146A. They bear several moderately large prickles which are about 0.5 to about 0.7 cms in length. The prickles are almost straight, angled slightly downward with a moderately short somewhat broad base; prickle color is between 165B and 164A. The major stem bears a few small prickles of similar shape and coloration.

The color of the branches is between 146A and 144A. They bear several moderately large prickles which are of similar size and shape to the large prickles on the major stems; prickle color is between 160B and 162B. The branches bear few small prickles of similar shape and coloration.

The color of the new shoots is between 144B and 147B often moderately suffused on the side facing the sun with between 183B and 178B. They bear several moderately large prickles which are of similar size and shape to the large prickles on the major stems; prickle color is near 144A often moderately suffused with between 183B and 178B. The shoots bear several small prickles of similar shape and coloration.

We claim:

1. A new and distinct variety of Shrub rose plant, substantially as described and illustrated herein.

* * * * *

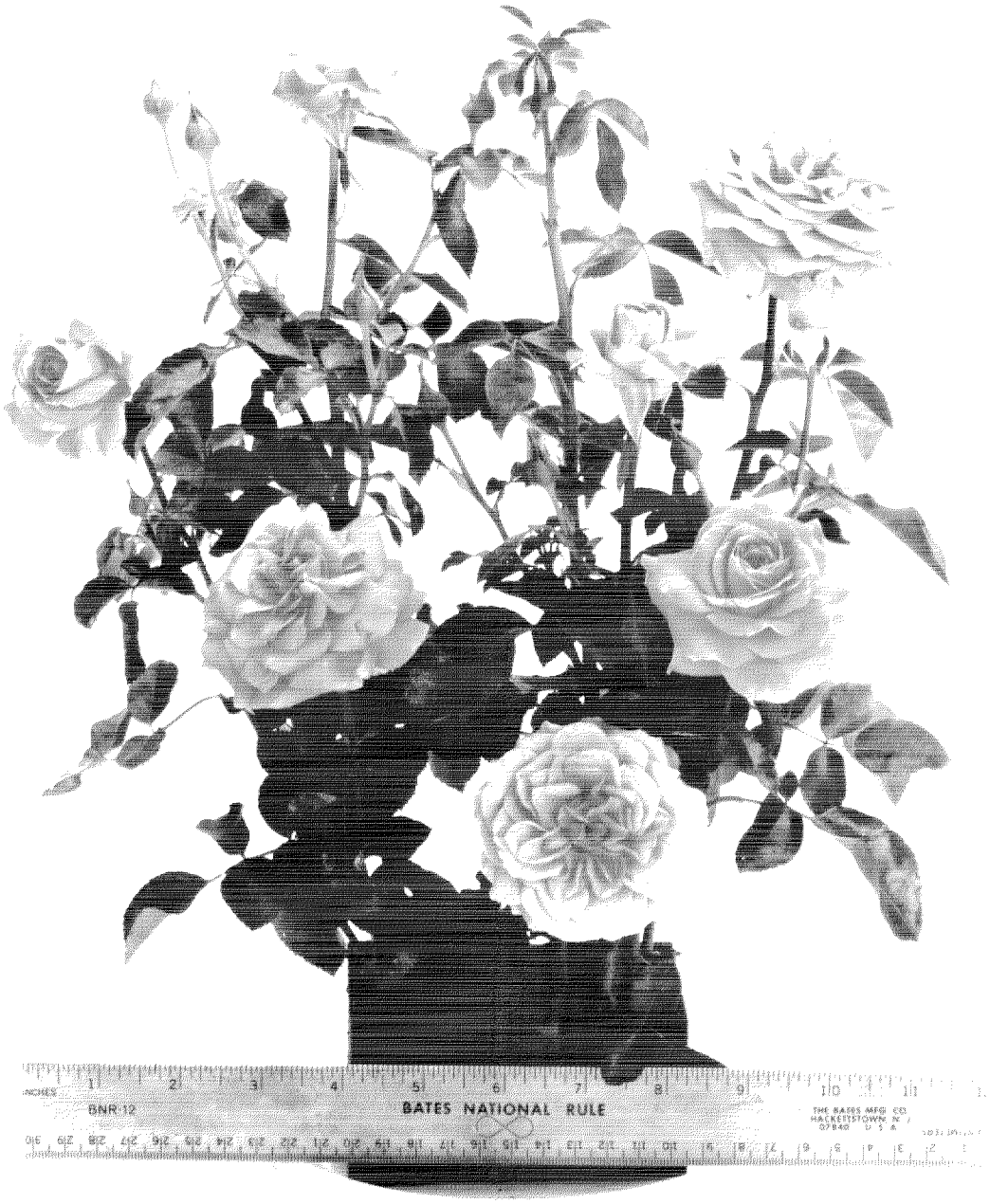
BNR 12
BATES NATIONAL RULE
THE BATES MFG CO
HACKETTSTOWN N J
07840 U S A